US006956127B2

(12) United States Patent
Shenai-Khatkhate et al.

(10) Patent No.: US 6,956,127 B2
(45) Date of Patent: Oct. 18, 2005

(54) ALKYL GROUP VA METAL COMPOUNDS

(75) Inventors: Deodatta Vinayak Shenai-Khatkhate, Danvers, MA (US); Michael Brendan Power, Newburyport, MA (US); Artashes Amamchyan, Wakefield, MA (US); Ronald L. DiCarlo, Jr., Newfields, NH (US)

(73) Assignee: Shipley Company, L.L.C., Marlborough, MA (US)

( * ) Notice: Subject to any disclaimer, the term of this patent is extended or adjusted under 35 U.S.C. 154(b) by 306 days.

(21) Appl. No.: 10/346,275

(22) Filed: Jan. 17, 2003

(65) Prior Publication Data

US 2003/0181746 A1 Sep. 25, 2003

Related U.S. Application Data

(63) Continuation-in-part of application No. 10/303,434, filed on Nov. 23, 2002, and a continuation-in-part of application No. 10/284,894, filed on Oct. 31, 2002.
(60) Provisional application No. 60/355,124, filed on Feb. 8, 2002, and provisional application No. 60/349,724, filed on Jan. 17, 2002.

(51) Int. Cl.[7] .............................. C07F 9/72; C07F 9/02; C07F 9/90; C23C 16/00; H01L 21/44
(52) U.S. Cl. .............................. 556/70; 568/8; 568/16; 427/587; 427/593; 438/604; 438/606; 438/681
(58) Field of Search .............................. 556/70; 568/8, 568/16; 427/587, 593; 438/604, 606, 681

(56) References Cited

U.S. PATENT DOCUMENTS

| 4,734,514 | A | 3/1988 | Melas et al. .................. 556/70 |
|---|---|---|---|
| 4,857,655 | A | 8/1989 | Valentine, Jr. ............... 556/70 |
| 5,003,093 | A | 3/1991 | Valentine, Jr. ............... 556/70 |
| 5,015,750 | A | 5/1991 | Tran et al. .................. 556/187 |
| 5,068,372 | A | 11/1991 | Kanjolia et al. .............. 556/70 |
| 5,892,120 | A | 4/1999 | Sugiya et al. .................. 568/8 |
| 6,660,874 | B2 | 12/2003 | Shenai-Khatkhate et al. . 556/70 |

FOREIGN PATENT DOCUMENTS

| EP | 0 356 095 | 2/1990 |
|---|---|---|
| EP | 0 579 248 | 4/1998 |
| EP | 0 839 817 | 5/1998 |
| EP | 0 560 029 | 7/1998 |
| EP | 1 001 049 | 5/2000 |
| GB | 1 344 051 | 1/1974 |
| JP | 6-87874 | 3/1994 |
| JP | 7-285977 | 10/1995 |
| JP | 10-130288 | 5/1998 |

OTHER PUBLICATIONS

Sekiguchi et al., "Auto–Doping of Carbon to Alas Grown by Metalorganic Chemical Vapor Deposition Using Trimethylaluminum and Tertiarybutylarsine", Japanese Journal of Applied Physics, Publication Office Japanese Journal of Applied Physics. Tokyo, JP. vol. 36, No. 5A, 1 May 1997 pp. 2638–2639, XP000732376, ISSN: 0021–4922.
Hashemi M M et al., "High Performance InP JFETs Grown by MOCVD Using Tertiarybutylphosphine", Journal of Electronic Materials, vol. 23, No. 2, 1994, pp. 233–237, XP009006937.
Feingold et al., "Rapid Thermal Low–Pressure Metal–organic Chemical Vapour Deposition (RT–LPMOCVD) of Semiconductor, Dielectric and Metal Film Onto InP and Related Materials", Materials Science and Engineering, vol. R13, 1994, pp. 57–104, XP009006936, ISSN: 0927–796X.
Takashi et al., "Organometallic Complexes Containing Antimony and Aluminum. I., Complex Formation of Alkylantimony compounds with aluminum compounds, AlET(n) Cl (3–n)", Journal of Organometallic Chemistry, vol. 8, 1967, pp. 209–223, XP009006880, ISSN: 0022–328X.
Dunhaupt, "Uber Wismutathl und Quecksilberathyl—Concerning ethyl bismuth and ethyl mercury", Liebigs Annalen Der Chemie, 1854, pp. 371–383, XP009006934, p. 376.
Marquardt, "Uber Wismuthalkyle—Concerning bismuth alkyls", Berichte Der Deutschen Chemischen Gesellschaft, vol. 20, 1887, pp. 1517–1523, XP009006939, ISSN: 0365–9496, pp. 1520–1521.
Database CA Online; Chemical Abstracts Service, Columbus, Ohio, U.S.; Ushikubo, Kohei et al.: "Purification of Organophosphorus Compounds for MOCVD (metalorganic chemical vapor deposition)" retrieved from STN Database accession No. 121:290435, XP002236818 & Kozan, vol. 47, No. 6, 1994, pp. 44–51, XP009006938, ISSN: 0287–9840.
Twamley et al., Sterically encumbered terphenyl substituted primary pnictanes ArEH2 and their metallated derivatives ArE (H) L1 (Ar=C6H3–2, 6–Trip2; Trip=2,4,6–triisopropylphenyl; E=N, P, As, Sb)–Journal of Organometallic Chemistry Elsevier–Sequoia S.A. Lausanne, CH, vol. 609, No. 1–2, Sep. 8, 2000, pp. 152–160, XP004331326, ISSN: 0022–328X, pp. 153–154.
Yang et al., "High Frequency and Low Noise C–doped GaInP/GaAs hetrojunction bipolar transistor grown by MOCVD Using TBA and TBP" Electronic Letters, vol. 32, No. 7, Mar. 28, 1996, pp. 689–671, XP006004960.

*Primary Examiner*—Porfirio Nazario-Gonzalez
(74) *Attorney, Agent, or Firm*—S. Matthew Cairns

(57) ABSTRACT

Disclosed are methods of preparing monoalkyl Group VA metal dihalide compounds in high yield and high purity by the reaction of a Group VA metal trihalide with an organo lithium reagent or a compound of the formula $R_nM^1X_{3-n}$, where R is an alkyl, $M^1$ is a Group IIIA metal, X is a halogen and n is an integer fro 1 to 3. Such monoalkyl Group VA metal dihalide compounds are substantially free of oxygenated impurities, ethereal solvents and metallic impurities. Monoalkyl Group VA metal dihydride compounds can be easily produced in high yield and high purity by reducing such monoalkyl Group VA metal dihalide compounds.

9 Claims, No Drawings

OTHER PUBLICATIONS

Kharasch et al., "Alkylation Reactions of Tetraethyllead. A new systhesis of ethyldichloroarsine and related compounds", Journal of Organic Chemistry, vol. 14, No. 3, May 1949, pp. 429–432, XP002236814, ISSN: 0022–3263.

Hendershot et al., "Synthesis characterization and chemical vapour deposition properties of primary and secondary neopentylstilbine. New antimony precursors for MOCVD", Chemistry of Materials, vol. 4, No. 4, 1992, pp. 833–837, XP002236815, ISSN 0897–4756.

King et al., "Poly(tertiary phosphines arnd arsines). XIII. Some neopentyl poly(tertiary phosphines)", Journal of Organic Chemistry, vol. 41, No. 6, 1976, pp. 972–977, XP002236816, p. 975, column 2.

Guillemin J–C et al., "Synthesis and characterization of ethylidynarsine", Journal of the American Chemical Society, vol. 116, No. 20, 1994, pp. 8930–8936, XP002236817, ISSN 0002–7863, p. 8930, column 2–p. 8931, column 1.

Zakharkin et al., "Synthesis of organometallic compounds from trialkylaluminum and metal salts", Bulletin of the Academy of Sciences of the USSR, Division of Chemical Sciences, 1959, pp. 1853–1858, XP00906879, ISSN: 0568–5230.

Inokin et al., "C–(N–N–Dialkylamino)–substituted arsaalkenes: a simple mthod for the preparation and examples of their reactivity", Phosphorus, Sulfur and Silicon, vol. 66, No. 14, 1992, pp. 257–260, XP009008986, p. 257.

Cowley et al., "Synthesis and Structure of a Diarsene: the first compound with an unsupported arsenic–arsenic double bond", Journal of the American Chemical Society, vol. 105, No. 16, 1983, pp. 5506–5507, XP002237393, p. 5506.

Twamley et al., "Homologous series of heavier element dipnictenes 2,6-Ar2H3C6E=EC6H3-2, 6-Ar2 (E=P, As, Sb, Bi; Ar=Mes=CgH2, 4,6-Me3; or Trip=CgH2-2,4, 6-iPr3) stabilized by m-terphenyl ligands", Journal of the American Chemical Society, vol. 121, No. 14, Apr. 14, 1999, pp. 3357–3367, XP002237394, pp. 3358–3359.

Chen et al., "Use of Tertiary Butyl Arsine for GaAs Growth", Applied Physics Letter; vol. 50 (4); Jan. 26, 1987; pp. 218–220.

Lum et al., Use of tertiarybutylarsine in the metalorganic chemical vapor deposition growth of GaAs; Applied Physics Letter; vol. 50 (5) Feb. 2, 1957; pp. 284–286.

John J. Eisch, "Organometallic Compounds of Group III. I. The Preparation of Gallium and Indium Alkyls from Organoaluminum Compounds", Journal of the American Chemical Society, vol. 84, No. 19, pp. 3605–3610, Oct. 17, 1962.

Stringfellow, Overview of the OMVPE Process, Organometallic Vapor Phase Epitaxy; Theory and Practice, Academic Press, $2^{nd}$ Edition, 1999.

Hagihara et al., Handbook of Organometallic Compounds, W.A. Benjamin, Inc., New York, 1968, pp. 560, 566, 571, 574 and 579–580.

ALKYL GROUP VA METAL COMPOUNDS

This application is a Continuation-in-Part of Non-Provisional application Ser. No. 10/303,434, filed Nov. 23, 2002 which application claims the benefit of Provisional Application Serial No. 60/355,124 filed Feb. 8, 2002 and a Continuation-in-Part of Non-Provisional application Ser. No. 10/284,894, filed Oct. 31, 2002 which application claims the benefit of Provisional Application Serial No. 60/349,725, filed Jan. 17, 2002.

BACKGROUND OF THE INVENTION

The present invention relates generally to the field of organometallic compounds. In particular, the present invention relates to monoalkyl Group VA metal compounds which are suitable for use as intermediates in the preparation of precursors for chemical vapor deposition.

Metal films may be deposited on surfaces, such as non-conductive surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), and chemical beam epitaxy ("CBE"). Chemical vapor deposition processes, such as metalorganic chemical vapor deposition ("MOCVD"), deposit a metal layer by decomposing organometallic precursor compounds at elevated temperatures, i.e. above room temperature, either at atmospheric pressure or at reduced pressures.

A wide variety of metals may be deposited using such CVD or MOCVD processes. See, for example, Stringfellow, *Organometallic Vapor Phase Epitaxy: Theory and Practice*, Academic Press, $2^{nd}$ Edition, 1999, for an overview of such processes. Organometallic compounds of arsenic, antimony, and bismuth are used to deposit epitaxial films in the semiconductor and related electronic industries. Epitaxial films such as gallium arsenide find applications in optoelectronic devices such as detectors, solar cells, light-emitting diodes ("LED's"), lasers and electronic switching devices such as field effect transistors ("FET's") and high electron mobility FET's ("HEMT's"). Ternary arsenic alloys also exist such as gallium indium arsenide ("GaInAs") and aluminum indium arsenide ("AlInAs"), which are more attractive than GaAs or aluminum gallium arsenide ("AlGaAs") for the most powerful fiber optic systems operating in the 1.3 to 1.55 micron wavelength range. Gallium arsenide phosphide ("GaAsP") is suitable for visible LED's and fiber optic emitters/detectors. Antimony and antimony alloy films are useful in fiber optics communication systems, particularly in the 1.3 and 1.55-micron regions. Antimony-containing semiconductor materials also have commercial applications including detection for seeker, night vision and surveillance devices (infrared detectors) and sources (LED's or lasers). A variety of binary, ternary and quaternary Group III/V semiconductor systems containing antimony have been evaluated for applications in infrared emitters and detectors operating in the 3 to 5 micron and 8 to 12 micron spectral ranges. These wavelength ranges are important since they are natural windows in the atmosphere for infrared transmission. Epitaxial antimony-based Group III/V semiconductors have potential applications in long wavelength detectors and high-speed electronic devices.

Arsine ("$AsH_3$") and phosphine ("$PH_3$") are attractive precursors for MOVPE since they provide arsenic and phosphorus along with hydrogen radicals that can scavenge any carbon-containing radicals generated during the MOVPE growth. However, the highly toxic nature of arsine and phosphine makes handling these gases in cylinders at high pressures dangerous. The threat of their rapid release in large quantities is serious and significantly high facility costs are often incurred to meet the appropriate safety requirements. Thus, there is a need to develop alternative Group VA hydride precursor compounds that are less hazardous than arsine and phosphine. Certain trialkyl Group VA metal compounds, such as trialkyl stibines, have been developed. However, such trialkyl compounds typically have low vapor pressures and higher decomposition temperatures. Such trialkyl compounds also result in carbon incorporation in the grown films. Monoalkyl Group VA dihydride compounds are excellent alternatives as they greatly reduce the amount of carbon incorporated in grown metal films.

For semiconductor and electronic device applications, these Group VA metal alkyls must be highly pure and be substantially free of detectable levels of both metallic impurities, such as silicon and zinc, as well as oxygenated impurities. Oxygenated impurities are typically present from the solvents used to prepare such organometallic compounds, and are also present from other adventitious sources of moisture or oxygen.

One method of preparing monoalkyl arsines and phosphines reacts arsine or phosphine gas with an alkene in the presence of a catalyst. See, for example, European Patent No. EP 579 248 B1 and European Patent Application No EP 560 029 A1. Another method reacts arsine with metallic sodium in liquid ammonia followed by reaction with an alkyl halide. See Magihara et al., *Handbook of Organometallic Compounds*, W. A. Benjamin, Inc., New York, 1968, pp 560, 566, 571, 574, and 579–580. Both of these approaches require the handling of arsine or phosphine, which are both very toxic.

Grignard type syntheses are also known. For example, arsenic trihalide or a phosphorus trihalide is reacted with an alkyl Grignard reagent to form monoalkyl arsenic or phosphorus dihalides which are subsequently reduced to form monoalkyl arsine or phosphine. See, for example, Japanese Patent Application No. JP 10-130 288. Such reactions are carried out in ethereal solvents. Other preparation methods utilizing ethereal solvents are known. See, for example, Japanese Patent Application No. JP 07-285977. The monoalkyl arsines and phosphines produced by these methods require extensive purification in order to remove the ethereal solvent. Even with such purification procedures, trace ethereal solvents remain in the monoalkyl arsines and phosphines.

Aluminum alkyls can have been used as reagents in the preparation of Group VA metal trialkyl compounds. For example, Zakharkin et al., *Bull. Acad. Sci. USSR*, 1959, p1853, discloses a method of producing trialkyl compounds of antimony and bismuth, as shown in equation (I), where R is ethyl, n-propyl or iso-butyl and X is chloride or fluoride.

$$MX_3 + R_3Al + \text{diethylether} \rightarrow MR_3 + AlX_3 \qquad (I)$$

Trace amounts of ethereal solvent invariably remain in the target organometallic compound obtained using conventional techniques. Such residual ethereal solvent contributes oxygen as a deleterious impurity in metal films deposited from such precursor compounds.

Attempts have been made to synthesize trialkyl Group VA organometallics in non-ethereal solvents. For example, Takashi et al., *J. Organometal. Chem.*, 8, pp 209–223, 1967, disclose the reaction of antimony trichloride with triethylaluminum in hexane. Such reaction was found to produce triethylstibine in extremely low yields (only about 10%), the remainder being about 42% metallic antimony and about 46% of an antimony-aluminum complex, (SbEt$_4$)(Al$_2$Et$_5$Cl$_2$). This article does not teach how to obtain triethylstibines free of antimony-aluminum complexes.

These trialkyl aluminum reaction approaches have been attempted only in the preparation of certain Group VA metal trialkyl compounds. Such approach has not been disclosed in the preparation of Group VA metal monoalkyl compounds.

Accordingly, there is a need for methods for preparing Group VA metal monoalkyls in high yields and for Group VA metal compounds substantially free of both metallic and oxygenated impurities for use as precursor compounds for CVD.

SUMMARY OF THE INVENTION

It has been found that monoalkyl Group VA metal dihalides can be prepared in high yield and in high purity starting from Group VA trihalides. Such reactions are carried out in ether-free solvents. Group VA monoalkyl dihalide compounds produced by this method are extremely pure and substantially free of oxygenated impurities.

It has been further found that Group VA metal monoalkyls can be prepared in high yield and in high purity by reducing alkyl Group VA dihalides in the presence of tertiary amines in hydrocarbon solvents. Group VA monoalkyl compounds produced by this method are extremely pure and substantially free of oxygenated impurities.

In one aspect, the present invention provides a method of preparing a monoalkyl Group VA metal dihalide compound including the step of reacting a Group VA metal trihalide with a reagent selected from the group consisting of a (C$_1$–C$_{10}$)alkyl lithium compound and a compound of the formula R$_n$M$^1$X$_{3-n}$ wherein each R is (C$_1$–C$_{10}$)alkyl, amino-substituted (C$_1$–C$_{10}$)alkyl, aryl or substituted aryl, M$^1$ is a Group IIIA metal, X is a halogen and n is an integer from 1 to 3, in an organic solvent free of oxygen substitution.

The present invention further provides a method for preparing a monoalkyl Group VA metal dihalide compound including the step of reacting a Group VA metal trihalide with a reagent selected from the group consisting of a (C$_1$–C$_{10}$)alkyl lithium compound and a compound of the formula R$_n$M$^1$X$_{3-n}$ wherein each R is (C$_1$–C$_{10}$)alkyl, amino-substituted (C$_1$–C$_{10}$)alkyl, aryl or substituted aryl, M$^1$ is a Group IIIA metal, X is a halogen and n is an integer from 1 to 3, in the presence of a tertiary amine in an organic solvent free of oxygen substitution.

Also provided by the present invention is a method for preparing a monoalkyl Group VA metal dihydride compound including the steps of: a) reacting a Group VA metal trihalide with a reagent selected from the group consisting of a (C$_1$–C$_{10}$)alkyl lithium compound and a compound of the formula R$_n$M$^1$X$_{3-n}$ wherein each R is (C$_1$–C$_{10}$)alkyl, amino-substituted (C$_1$–C$_{10}$)alkyl, aryl or substituted aryl, M$^1$ is a Group IIIA metal, X is a halogen and n is an integer from 1 to 3, in an organic solvent free of oxygen substitution to from a monoalkyl Group VA metal dihalide; and b) reducing the monoalkyl Group VA metal dihalide in the presence of a tertiary amine in an organic solvent free of oxygen substitution.

In one embodiment, the present invention provides a method for preparing monoalkyl Group VA metal compounds including the step of reducing a monoalkyl Group VA metal dihalide in the presence of a tertiary amine in an organic solvent that is free of oxygen substitution.

In another embodiment, the present invention provides a method for depositing a film of a Group VA metal on a substrate including the steps of: a) conveying a Group VA metal source compound in the gaseous phase to a deposition chamber containing the substrate; b) decomposing the Group VA metal source compound in the deposition chamber; and c) depositing a film of the Group VA metal on the substrate; wherein the Group VA metal source compound is prepared by the method including the step of reducing a monoalkyl Group VA metal dihalide in the presence of a tertiary amine in an organic solvent that is free of oxygen substitution.

In a further embodiment, the present invention provides a method for manufacturing an electronic device including the step of depositing a film of a Group VA metal on an electronic device substrate including the steps of: a) conveying a Group VA metal compound in the gaseous phase to a deposition chamber containing the substrate; b) decomposing the Group VA metal compound in the deposition chamber; and c) depositing a film of the Group VA metal on the substrate; wherein the Group VA metal compound is prepared by the method including the step of reducing a monoalkyl Group VA metal dihalide in the presence of a tertiary amine in an organic solvent that is free of oxygen substitution.

DETAILED DESCRIPTION OF THE INVENTION

As used throughout this specification, the following abbreviations shall have the following meanings, unless the context clearly indicates otherwise: ° C.=degrees centigrade; NMR=nuclear magnetic resonance; mol=moles; b.p.=boiling point, g=gram; L=liter; M=molar; ca.=approximately; μm=micron=micrometer; and mL=milliliter.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Unless otherwise noted, all amounts are percent by weight and all ratios are molar ratios. All numerical ranges are inclusive and combinable in any order except where it is clear that such numerical ranges are constrained to add up to 100%.

In one embodiment, the present invention provides a method for preparing monoalkyl Group VA metal dihalide compounds including the step of reacting a Group VA metal trihalide with a reagent selected from the group consisting of an organolithium reagent and a compound of the formula R$_n$M$^1$X$_{3-n}$ wherein each R is (C$_1$–C$_{10}$)alkyl, amino-substituted (C$_1$–C$_{10}$)alkyl, aryl or substituted aryl, M$^1$ is a Group IIIA metal, X is a halogen and n is an integer from 1 to 3, in an organic solvent free from oxygen substitution. Any Group VA metal trihalide may be used. Such trihalide compounds have the formula MX$_3$ wherein M is a Group VA metal and each X is independently chlorine, bromine, fluorine or iodine. Suitable Group VA metals include antimony ("Sb"), arsenic ("As"), bismuth ("Bi") and phosphorus ("P"), and preferably arsenic and phosphorus. Preferably, the halogen is chlorine, bromine or iodine.

Particularly suitable Group VA metal trihalide compounds include, but are not limited to, antimony trichloride, antimony tribromide, antimony triiodide, arsenic trichloride, arsenic tribromide, arsenic triiodide, bismuth trichloride, bismuth tribromide, bismuth triiodide, phosphorus trichloride, phosphorus tribromide, phosphorus triiodide, and mixtures thereof. Group VA metal trichlorides are more preferred. It will be appreciated that mixed halide compounds may also be advantageously used in the present invention. Such Group VA metal trihalides are generally commercially available from a variety of sources or may be prepared by a variety of methods known in the literature.

A wide variety of Group IIIA compounds may be used. Suitable Group IIIA compounds useful in the present invention include, but are not limited to, compounds that have the formula $R_nM^1X_{3-n}$, wherein each R is independently selected from $(C_1-C_{10})$alkyl, amino-substituted $(C_1-C_{10})$ alkyl, aryl or substituted aryl; $M^1$ is a Group IIIA metal; X is halogen; and n is an integer from 1 to 3. Any aryl group that does not contain oxygen is suitable for R, such as, but not limited to, phenyl, naphthyl, biphenyl and the like. It is preferred that R is $(C_1-C_{10})$alkyl or amino-substituted $(C_1-C_{10})$alkyl, more preferably $(C_1-C_8)$alkyl, and still more preferably $(C_1-C_6)$alkyl. $M^1$ is suitably boron, aluminum, gallium, indium or thallium and preferably aluminum or gallium. Preferably, X is selected from fluorine, chlorine or bromine. By "amino-substituted $(C_1-C_{10})$alkyl" it is meant that one or more hydrogens on the alkyl group is replaced by amino ("NH$_2$"), $(C_1-C_6)$alkylamino ("R$^2$NH") or di $(C_1-C_6)$alkylamino ("(R$^2$)$_2$N"), where $R^2$ represents the alkyl group. By "substituted aryl" it is meant that one or more hydrogens on the aryl group is replaced by $(C_1-C_6)$ alkyl, amino, $(C_1-C_6)$alkylamino or di $(C_1-C_6)$alkylamino.

In one embodiment, it is preferred that n is 3. Such Group IIIA compounds where n is 3 include trialkylboron, trialkylaluminum, dialkylaluminum halide, trialkylgallium, trialkylindium and trialkylthallium, with trialkylaluminum and trialkylgallium compounds being preferred. In an alternate embodiment, it is preferred that n is 1 or 2. Such Group IIIA compounds where n is 1–2 include dialkylaluminum chlorides. Suitable Group IIIA compounds are generally commercially available from a variety of sources or may be prepared by a variety of methods known in the literature.

A wide variety of organolithium compounds may be used to prepare the monoalkyl Group VA metal dihalides. Such organo lithium compounds typically have the formula $R^1Li$ where $R^1$ is $(C_1-C_{10})$alkyl, aryl or $(C_1-C_6)$alkyl-substituted aryl. The term "$(C_1-C_6)$alkyl-substituted aryl" refers to an aryl having one or more of its hydrogens replaced with a $(C_1-C_6)$alkyl substituent. "Aryl" refers to any aromatic moiety, and preferably an aromatic hydrocarbon. Exemplary aryl moieties include phenyl, tolyl, xylyl, naphthyl, biphenyl, benzyl, and the like. As used herein, "aryl" includes $(C_1-C_6)$alkaryls such as benzyl, phenethyl, phenyl propyl and the like. Particularly suitable groups for $R^1$ include, but are not limited to, methyl, ethyl, n-propyl, iso-propyl, n-butyl, iso-butyl, sec-butyl, tert-butyl, cyclopentyl, cyclohexyl, methylcyclohexyl, phenyl, tolyl, benzyl, and the like. Preferred alkyls include, methyl, ethyl, n-propyl, iso-propyl, tert-butyl and iso-butyl. In a particular embodiment, when an aryl lithium compound is used a tertiary amine is also used in the preparation of the Group VA metal dihalide compound. The organo lithium compounds are generally commercially available, such as from Aldrich Chemical, Milwaukee, Wis., or may be prepared by methods known in the art.

A wide variety of organic solvents may be used in the preparation of the monoalkyl Group VA metal dihalides, provided that such organic solvents do not contain oxygenated species. It is further preferred that the organic solvents do not contain dissolved oxygen. Particularly suitable organic solvents include, but are not limited to, hydrocarbons and aromatic hydrocarbons. Preferred organic solvents include benzene; alkyl substituted benzenes such as toluene, xylene, and $(C_4-C_{20})$alkyl benzenes such as $(C_{10}-C_{12})$alkyl benzenes and $(C_{10}-C_{20})$alkyl biphenyls; and aliphatic hydrocarbons such as pentane, hexane, heptane, octane, decane, dodecane, squalane, cyclopentane, cyclohexane, and cycloheptane; and mixtures thereof. More preferably, the organic solvent is benzene, toluene, xylene, $(C_4-C_{20})$ alkyl benzenes, hexane, heptane, cyclopentane or cyclohexane. It will be appreciated that more than one organic solvent may be advantageously used. In an alternative embodiment, the tertiary amine may be used as the organic solvent. Such organic solvents are generally commercially available from a variety of sources. Such solvents may be used as is or, preferably, purified prior to use.

Preferably, such organic solvents are deoxygenated prior to use. The solvents may be deoxygenated by a variety of means, such as purging with an inert gas, degassing the solvent in vacuo, or a combination thereof. Suitable inert gases include argon, nitrogen and helium, and preferably argon or nitrogen.

In an alternate embodiment, the reaction of the Group VA metal trihalide with the organolithium compound or the compound of the formula $R_nM^1X_{3-n}$ wherein R, $M^1$, X and n are as defined above, may be carried out in the presence of a tertiary amine. In particular, a tertiary amine is used when an aryl lithium compound is used. Under certain conditions, such as when a one-pot synthesis of a monoalkyl Group VA metal dihydride is desired, it is preferred that a tertiary amine is used.

Any tertiary amine may suitably be used. Suitable tertiary amines include, but are not limited to, poly(tertiary amines) and amines having the general formula $NR^4R^5R^6$, wherein $R^4$, $R^5$ and $R^6$ are independently selected from $(C_1-C_6)$ alkyl, di$(C_1-C_6)$alkylamino-substituted $(C_1-C_6)$alkyl, and phenyl and wherein $R^4$ and $R^5$ may be taken together along with the nitrogen to which they are attached to form a 5–7 membered heterocyclic ring. Such heterocyclic ring may be aromatic or non-aromatic. Particularly suitable tertiary amines include, but are not limited to: trimethylamine; triethylamine; tri-n-propylamine; tri-n-butylamine; tri-iso-propylamine; tri-iso-butylamine; dimethylaminocyclohexane; diethylaminocyclohexane; dimethylaminocyclopentane; diethylaminocyclopentane; N-methylpyrrolidine; N-ethylpyrrolidine; N-n-propylpyrrolidine; N-iso-propylpyrrolidine; N-methylpiperidine; N-ethylpiperidine; N-n-propylpiperidine; N-iso-propylpiperidine; N,N'-dimethylpiperazine; N,N'-diethylpiperazine; N,N'-dipropylpiperazine; N,N,N',N'-tetramethyl-1,2-diaminoethane; pyridine; pyrazine; pyrimidine; N,N,N',N'-tetramethylethylene diamine; N,N,N',N'-tetraethylethylene diamine; N,N,N',N'-tetramethylpropylenediamine; N,N,N', N'-tetraethylpropylene diamine; N,N,N',N'-tetramethylbutylene diamine; N,N,N',N'-tetraethylbutylene diamine; 1,5-tetramethyldiaminopentane; 1,5-tetraethyldiaminopentane; N,N,N',N'-tetramethylhexamethylene diamine; 1,7-tetramethyldiaminoheptane; 1,7-tetraethyldiaminoheptane; 1,8-tetramethyldiaminooctane; 1,8-tetraethyldiaminooctane; 1,9-tetramethyldiaminononane; 1,9-tetraethyldiaminononane; 1,10-tetramethyldiaminodecane; 1,10-tetraethyldiaminodecane; 1,12-tetramethyldiaminododecane; 1,12-tetraethyldiaminododecane; pentamethyl diethylenetriamine; and mixtures thereof. Preferred amines include trimethylamine, triethylamine, tri-n-propylamine, tri-iso-propylamine, and tri-n-butylamine. More preferably, the tertiary amine is triethylamine or tri-n-propylamine. It will be appreciated by those skilled in the art that more than one tertiary amine may be used in the present invention. Such tertiary amines are generally commercially available from a variety of sources. Such tertiary amines may be used as is or, preferably further purified prior to use.

In the process of the present invention, the Group IIIA compound or organolithium compound, an organic solvent and optional tertiary amine may be combined in any order prior to reacting with the Group VA metal trihalide. Preferably, the Group IIIA compound is first combined with the tertiary amine to form an amine-Group IIIA adduct. Typically, the amine-Group IIIA adduct may be formed at a wide variety of temperatures. Suitable temperatures for forming the adduct are from −78° to 90° C., although lower or higher temperatures may be suitably employed. The Group VA metal trihalide is then reacted with the amine-Group IIIA adduct to form the desired trialkyl Group VA metal compound. It is preferred that the Group VA metal trihalide is added dropwise, either neat or as a hydrocarbon solution, to an amine-Group IIIA adduct or organo lithium compound. Suitable temperatures to form the monoalkyl Group VA dihalide compound are typically from −78° to 80° C. and preferably from −78° C. to ambient.

In an alternate embodiment, the present invention provides a method for preparing monoalkyl Group VA metal dihalide compounds including the steps of reacting a Group IIIA compound with a tertiary amine to form an amine-Group IIIA adduct in an organic solvent that is free of oxygenated species; and reacting the amine-Group IIIA adduct with a Group VA metal trihalide in the organic solvent.

In a further embodiment, the present invention provides a method of preparing a monoalkyl Group VA metal dihalide compound including the step of reacting a Group VA metal trihalide with a reagent selected from the group consisting of an alkyl lithium compound and a compound of the formula $RnM^1X_{3-n}$, wherein R, $M^1$, X and n are as defined above, in the presence of a tertiary amine in an organic solvent free of oxygen substitution.

In general, the tertiary amine is present in a stoichiometric amount to the Group IIIA compound or the organo lithium compound. The molar ratio Group VA metal trihalide to Group IIIA compound is typically 0.8:1 to 2.2:1, and preferably 1:1 to 2:1, with the exact stoichiometry being dependent on the nature of Group IIIA compound, Group VA compound, and the tertiary amine selected. The molar ratio of Group IIIA to Group VA Compound ranges from 0.5 to 1.0. The organo lithium compound and the Group VA metal trihalide are typically present in a molar ratio of 0.8:1 to 1:0.8, preferably from 0.9:1 to 1:0.9, and more preferably 1:1.

The specific tertiary amine and organic solvent used depend upon the particular monoalkyl Group VA dihalide compound desired. For example, the organic solvent and tertiary amine may be selected such that they are more volatile or less volatile than the desired monoalkyl Group VA dihalide compound. Such differences in volatility provide easier separation of the monoalkyl Group VA dihalide compound from both the amine and organic solvent. The monoalkyl Group VA dihalide compounds of the present invention may be suitably purified by known techniques, such as recrystallization or distillation.

Exemplary monoalkyl Group VA metal dihalides include, but are not limited to, those having the general formula $RMX_2$, wherein R is $(C_1-C_{10})$alkyl, amino-substituted $(C_1-C_{10})$alkyl, aryl or substituted aryl; M is a Group VA metal; and each X is independently fluorine, chlorine, bromine or iodine. Arsenic and phosphorus are the preferred Group VA metals. It is preferred that X is chlorine, bromine or iodine. It is preferred that R is $(C_1-C_8)$alkyl, and more preferably $(C_1-C_6)$alkyl.

Particularly suitable monoalkyl Group VA metal dihalides include, but are not limited to, methyl arsenic dichloride, ethyl arsenic dichloride, n-propyl arsenic dichloride, iso-propyl arsenic dichloride, n-butyl arsenic dichloride, iso-butyl arsenic dichloride, tert-butyl arsenic dichloride, cyclo-hexyl arsenic dichloride, methylcyclohexyl arsenic dichloride, methyl arsenic dibromide, ethyl arsenic dibromide, n-propyl arsenic dibromide, iso-propyl arsenic dibromide, n-butyl arsenic dibromide, iso-butyl arsenic dibromide, tert-butyl arsenic dibromide, cyclohexyl arsenic dibromide, methyl phosphorus dichloride, ethyl phosphorus dichloride, n-propyl phosphorus dichloride, iso-propyl phosphorus dichloride, n-butyl phosphorus dichloride, iso-butyl phosphorus dichloride, tert-butyl phosphorus dichloride, cyclopentyl phosphorus dichloride, cyclohexyl phosphorus dichloride, methyl phosphorus dibromide, ethyl phosphorus dibromide, n-propyl phosphorus dibromide, iso-propyl phosphorus dibromide, n-butyl phosphorus dibromide, iso-butyl phosphorus dibromide, tert-butyl phosphorus dibromide, cyclohexyl phosphorus dibromide, methylcyclohexyl phosphorus dibromide, and mixtures thereof. It will be appreciated that mixed halide compounds may also be advantageously used in the present invention. Such monoalkyl Group VA metal dihalides are generally commercially available from a variety of sources or may be prepared by a variety of methods known in the literature.

The present monoalkyl Group VA metal dihalide compounds may be used as precursors in the vapor phase deposition of Group VA metals and alloys thereof. Such compounds are particularly useful as intermediates in the preparation of other vapor phase deposition precursors, such as monoalkyl Group VA metal dihydride compounds.

In another embodiment, the present invention provides a method for preparing monoalkyl Group VA metal dihydride compounds including the step of reducing a monoalkyl Group VA metal dihalide in the presence of a tertiary amine in an organic solvent that is free of oxygen substitution. Any of the above described monoalkyl Group VA metal dihalide compounds may be used, but other Group VA metal dihalide compounds may also be used. Other suitable monoalkyl Group VA dihalides include those having the formula $X_2M^1R^1M^2X_2$, wherein $M^1$ and $M^2$ are independently selected from arsenic and phosphorus, each X is independently selected from fluorine, chlorine, bromine and iodine, and $R^1$ is an alkylene or arylene group. It is preferred that the groups for $R^1$ are free of oxygen substitution. Suitable groups for $R^1$ include, but are not limited to: $(C_1-C_{10})$ alkylene such as methylene, ethylene, propylene, butylene and the like; $(C_8-C_{20})$aralkylene such as p-xylylene; $(C_6-C_{20})$arylene such as phenylene, biphenylene and naphthylene; and the like.

These dihydride compounds are suitably prepared by reducing the monoalkyl Group VA metal dihalide compounds in the presence of a tertiary amine in an organic solvent free of oxygen substitution. In general, the monoalkyl Group VA metal dihydride compounds are prepared from monoalkyl Group VA dihalides according to the following reaction scheme:

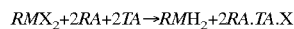

wherein $RMX_2$ is the monoalkyl Group VA dihalide compound as described above, RA is a reducing agent, TA is a tertiary amine, $RMH_2$ is a monoalkyl Group VA dihydride where R is as defined above for the monoalkyl Group VA metal dihalide compounds and RA.TA.X is a reducing agent-tertiary amine-halide salt.

Suitable tertiary amines useful in the reduction of the monoalkyl Group VA metal dihalide compounds are those described above. The organic solvents suitable are also those described above. A wide variety of reducing agents may be used in the present invention. Particularly useful reducing agents include borohydride reducing agents such as sodium borohydride and lithium borohydride; aluminum hydride reducing agents such as lithium aluminum hydride and $NaAlH_2(OCH_2CH_2OCH_3)_2$; borane reducing agents such as dimethylamine borane, cyclohexylamine borane, morpholine borane, and the like. Aluminum hydride reducing agents are preferred.

In the preparation of monoalkyl Group VA metal dihydrides, the tertiary amine, organic solvent and reducing agent may be combined in any order prior to reacting with the monoalkyl Group VA metal dihalide. Typically, the reduction may be performed at a wide range of temperatures. It is preferred that a monoalkyl Group VA metal dihalide is added dropwise, either neat or as a hydrocarbon solution, to an amine-reducing agent mixture. Suitable temperatures for forming the monoalkyl Group VA dihydrides of the present invention are from below ambient temperature to about 90° C.

In general, the tertiary amine is present in twice the molar amount of the monoalkyl Group VA metal dihalide compound, although other suitable amounts may be used. The amount of reducing agent is typically also present in twice the molar amount of monoalkyl Group VA dihalide compound, but other suitable amounts may be used.

The specific tertiary amine and organic solvent used depend upon the particular monoalkyl Group VA dihydride compound desired. For example, the organic solvent and tertiary amine may be selected such that they are more volatile or less volatile than the desired monoalkyl Group VA dihydride compound. Such differences in volatility provide easier separation of the monoalkyl Group VA dihydride compound from both the amine and organic solvent. The monoalkyl Group VA dihydride compounds thus produced may be suitably purified by a variety of techniques, such as, but not limited to, distillation, recrystallization or mixtures of such techniques.

A wide variety of monoalkyl Group VA metal dihydride compounds may be produced by the present invention. Accordingly, the monoalkyl Group VA metal dihydride compounds have the formula $RMH_2$, wherein M is a Group VA metal; and R is $(C_1-C_{10})$alkyl, amino-substituted $(C_1-C_{10})$alkyl, aryl or substituted aryl. The terms "substituted aryl" and "amino-substituted $(C_1-C_{10})$alkyl " are as defined above. It is preferred that monoalkyl arsines (i.e. $RAsH_2$) and monoalkyl phosphines (i.e. $RPH_2$) are produced by this method. Particularly useful monoalkyl arsines and monoalkyl phosphines are $(C_1-C_6)$alkyl arsines and $(C_1-C_6)$ alkyl phosphines. Suitable monoalkyl arsines and monoalkyl phosphines include, but are not limited to: methyl arsine, ethyl arsine, n-propyl arsine, iso-propyl arsine, n-butyl arsine, iso-butyl arsine, tert-butyl arsine, cyclohexyl arsine, methylcyclohexyl arsine, cyclopentyl arsine, methyl phosphine, ethyl phosphine, n-propyl phosphine, iso-propyl phosphine, n-butyl phosphine, iso-butyl phosphine, tert-butyl phosphine, cyclohexyl phosphine, methylcyclohexyl phosphine, cyclopentyl phosphine, and the like. Other suitable compounds include, but are not limited to, phenyl arsine, phenyl phosphine, dimethylaminophenyl arsine, and dimethylaminophenyl phosphine.

In an alternate embodiment, suitable monoalkyl Group VA metal dihydrides produced by the present invention include, but are not limited to: bisphosphino methane ($H_2PCH_2PH_2$); 1,2-bisphosphino ethane ($H_2PCH_2CH_2PH_2$); 1,3-bisphosphino propane ($H_2PCH_2CH_2CH_2PH_2$); bisphosphino benzenes ($H_2PC_6H_4PH_2$) such as 1,4-bisphosphino benzene and 1,2-bisphosphino benzene; 1,4-bisphosphinomethyl benzene ($H_2PCH_2C_6H_4CH_2PH_2$); bisarseno methane ($H_2AsCH_2AsH_2$), bisarseno ethane ($H_2AsCH_2CH_2AsH_2$), 1,3-bisarseno propane ($H_2AsCH_2CH_2CH_2AsH_2$), bisarseno benzenes ($H_2AsCH_6H_4AsH_2$), and the like.

An advantage of the present invention is that monoalkyl Group VA dihydride compounds can be prepared that are substantially free of ethereal solvents, and preferably free of ethereal solvents. A further advantage is that such monoalkyl Group VA dihydride compounds are substantially free of metallic impurities such as zinc and silicon, and preferably free of silicon and zinc. By "substantially free" it is meant that the compounds contain less than 0.5 ppm of such impurities, and preferably less than 0.25 ppm. Thus, monoalkyl Group VA metal dihydride compounds prepared from monoalkyl Group VA metal dihalide compounds are substantially free of zinc and silicon, and preferably free of zinc, silicon, and ethereal solvents. These compounds are typically liquids at room temperature and provide safer alternatives to conventional gaseous arsine and phosphine for use as precursors for vapor phase deposition of Group VA metals.

The monoalkyl Group VA metal dihydride compounds are particularly suitable for use as precursors in CVD, and particularly MOCVD and metalorganic vapor phase epitaxy ("MOVPE"), particularly for MOVPE of compound semiconductors. These compounds are useful for depositing gallium arsenide films, indium phosphide films, aluminum gallium arsenide films, and the like. Such films are useful in the manufacture of electronic devices, such as integrated circuits, and optoelectronic devices.

Films of Group VA metals are typically deposited by first placing the desired monoalkyl Group VA metal compound, i.e. source compound or precursor compound, in a bubbler having an outlet connected to a deposition chamber. Suitable monoalkyl Group VA metal compounds include the present monoalkyl Group VA metal dihalides as well as the present monoalkyl Group VA metal dihydrides. A wide variety of bubblers may be used, depending upon the particular deposition apparatus used. The source compound is maintained in the bubbler as a liquid or solid. Solid source compounds are typically vaporized or sublimed prior to transportation to the deposition chamber. The source compound is typically transported to the deposition chamber by passing a carrier gas through the bubbler. Suitable carrier gasses include nitrogen, hydrogen, and mixtures thereof. In general, the carrier gas is introduced below the surface of the source compound, and bubbles up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The typical deposition chamber temperature is from 300° to 1200° C., the exact temperature selected being optimized to provide efficient deposition. Optionally, the temperature in the deposition chamber as a whole can be reduced if the substrate is maintained at an elevated temperature, or if other energy such as radio frequency ("RF") energy is generated by an RF source.

Suitable substrates for deposition, in the case of electronic device manufacture, may be silicon, gallium arsenide, indium phosphide, and the like. Such substrates are particularly useful in the manufacture of integrated circuits.

Deposition is continued for as long as desired to produce a film having the desired properties. Typically, the film thickness will be from several hundred to several thousand angstroms or more when deposition is stopped.

Thus, the present invention provides a method for depositing a film of a Group VA metal on a substrate including the steps of: a) conveying a monoalkyl Group VA metal dihalide source compound in the gaseous phase to a deposition chamber containing the substrate; b) decomposing the monoalkyl Group VA metal dihalide source compound in the deposition chamber; and c) depositing a film of the Group VA metal on the substrate.

The present invention further provides a method for manufacturing an electronic device including the step of depositing a film of a Group VA metal on an electronic device substrate including the steps of: a) conveying a monoalkyl Group VA metal dihalide source compound in the gaseous phase to a deposition chamber containing the substrate; b) decomposing the monoalkyl Group VA metal dihalide source compound in the deposition chamber; and c) depositing a film of the Group VA metal on the substrate.

In another embodiment, the present invention provides a method for depositing a film of a Group VA metal on a substrate including the steps of: a) conveying a monoalkyl Group VA metal dihydride source compound in the gaseous phase to a deposition chamber containing the substrate; b) decomposing the monoalkyl Group VA metal dihydride source compound in the deposition chamber; and c) depositing a film of the Group VA metal on the substrate; wherein the Group VA metal compound is prepared by the method including the step of reducing a monoalkyl Group VA metal dihalide in the presence of a tertiary amine in an organic solvent that is free of oxygen substitution. In an alternate embodiment, the present invention provides a method for depositing a film of a Group VA metal on a substrate including the steps of: a) conveying a Group VA metal compound of the formula $RMH_2$ or $H_2MR^1 MH_2$ in the gaseous phase to a deposition chamber containing the substrate; b) decomposing the Group VA metal compound in the deposition chamber; and c) depositing a film of the Group VA metal on the substrate; wherein the Group VA metal compound is substantially free of ethereal solvents; and wherein R is $(C_1-C_{10})$alkyl, amino-substituted $(C_1-C_{10})$alkyl, aryl or substituted aryl; $R^1$ is $(C_1-C_{10})$alkylene, $(C_8-C_{20})$aralkylene or $(C_6-C_{20})$arylene; and M is arsenic or phosphorus. In still another embodiment, the present invention provides a method for depositing a film of a Group VA metal on a substrate including the steps of: a) conveying a monoalkyl Group VA metal dihydride compound in the gaseous phase to a deposition chamber containing the substrate; b) decomposing the monoalkyl Group VA metal dihydride compound in the deposition chamber; and c) depositing a film of the Group VA metal on the substrate; wherein the monoalkyl Group VA metal dihydride compound is substantially free of ethereal solvents; and wherein the monoalkyl Group VA metal dihydride compound is selected from the group consisting of methyl arsine, ethyl arsine, n-propyl arsine, iso-propyl arsine, n-butyl arsine, iso-butyl arsine, tert-butyl arsine, cyclohexyl arsine, cyclopentyl arsine, methyl phosphine, ethyl phosphine, n-propyl phosphine, iso-propyl phosphine, n-butyl phosphine, iso-butyl phosphine, tert-butyl phosphine, cyclohexyl phosphine, cyclopentyl phosphine, and mixtures thereof.

In a further embodiment, the present invention further provides a method for manufacturing an electronic device including the step of depositing a film of a Group VA metal on an electronic device substrate including the steps of: a) conveying a monoalkyl Group VA metal dihydride source compound in the gaseous phase to a deposition chamber containing the substrate; b) decomposing the monoalkyl Group VA metal dihydride source compound in the deposition chamber; and c) depositing a film of the Group VA metal on the substrate; wherein the monoalkyl Group VA metal dihydride source compound is prepared by the method including the step of reducing a monoalkyl Group VA metal dihalide in the presence of a tertiary amine in an organic solvent that is free of oxygen substitution. In still another embodiment, the present invention provides a method for manufacturing an electronic device including the step of depositing a film of a Group VA metal on an electronic device substrate including the steps of: a) conveying a Group VA metal compound of the formula $RMH_2$ or $H_2MR^1 MH_2$ in the gaseous phase to a deposition chamber containing the substrate; b) decomposing the Group VA metal compound in the deposition chamber; and c) depositing a film of the Group VA metal on the substrate; wherein the trimethyl Group VA metal compound is substantially free of ethereal solvents and wherein R is $(C_1-C_{10})$alkyl, amino-substituted $(C_1-C_{10})$alkyl, aryl or substituted aryl; $R^1$ is $(C_1-C_{10})$alkylene, $(C_8-C_{20})$aralkylene or $(C_6-C_{20})$arylene; and M is arsenic or phosphorus. In yet a further embodiment, the present invention provides a method for manufacturing an electronic device including the step of depositing a film of a Group VA metal on an electronic device substrate including the steps of: a) conveying a monoalkyl Group VA metal dihydride compound in the gaseous phase to a deposition chamber containing the substrate; b) decomposing the monoalkyl Group VA metal dihydride compound in the deposition chamber; and c) depositing a film of the Group VA metal on the substrate; wherein the monoalkyl Group VA metal dihydride compound is substantially free of ethereal solvents, wherein the Group VA metal compound is selected from the group consisting of methyl arsine, ethyl arsine, n-propyl arsine, iso-propyl arsine, n-butyl arsine, iso-butyl arsine, tert-butyl arsine, cyclohexyl arsine, cyclopentyl arsine, methyl phosphine, ethyl phosphine, n-propyl phosphine, iso-propyl phosphine, n-butyl phosphine, iso-butyl phosphine, tert-butyl phosphine, cyclohexyl phosphine, cyclopentyl phosphine, and mixtures thereof.

Suitable electronic devices include, but are not limited to, integrated circuits and light emitting diodes ("LEDs").

The following examples are presented to illustrate further various aspects of the present invention, but are not intended to limit the scope of the invention in any aspect. All manipulations are performed in an inert atmosphere, typically under an atmosphere of dry nitrogen.

EXAMPLE 1

Tert-butyl phosphorous dichloride is prepared by adding an equimolar amount of a solution of tert-butyl lithium in pentane to a solution of phosphorus trichloride in a mixture of $(C_{10}-C_{12})$ linear alkyl benzenes ("LAB"). After allowing the compounds to completely react, the pentane is removed by atmospheric pressure distillation. Solid tert-butyl phosphorus dichloride containing ca. 8% of di-tert-butyl derivative is then obtained by vacuum sublimation directly from the reaction mixture.

EXAMPLE 2

Ethyl arsenic dichloride is prepared by alkyl group exchange. Triethyl aluminum (25, 0.22 mol) is added dropwise via a pressure equalizing addition funnel to a cooled solution (−78° C., dry ice/iso-propanol) of arsenic trichloride (79.4 g, 0.44 mol) in 100 g of degassed pentane. An exothermic reaction takes place with white fumes forming a pressure pulse occurring coinciding with each drop added. The complete addition takes ca. 1.5 hours. The mixture is then warmed to room temperature to yield two layers in the reaction vessel, a yellow bottom layer and a clear upper layer. The pentane layer is then removed under full vacuum (ca. $10^{-3}$ Torr) at ambient temperature. After the pentane is distilled off, the reaction mixture is again vacuum distilled (ca. $10^{-3}$ Torr) at ca. 50° C. A clear liquid is condensed in a cooled (−78° C., dry ice) receiving flask. The clear liquid is analyzed by NMR spectroscopy and is found to be ethyl arsenic dichloride. An amount of 30 g of product is obtained.

EXAMPLE 3 t-Butylphosphorus dichloride is prepared by dropwise addition of 330 mL of 1.7 M tert-butyllithium solution in pentane to a chilled (−78° C.) solution of 75.5 g phosphorus trichloride in 350 mL degassed pentane. Upon complete addition the reaction mixture is allowed to warm up to room temperature and stirred for 4 hours. The solids are removed by filtration and washed with pentane. Combined pentane fractions are subjected to atmospheric pressure distillation. Subsequent vacuum sublimation of the residue yielded 57 g (65%) of tert-butylphosphorus dichloride in the form of colorless solid material. In addition, the product contains ca. 7% of di-tert-butylphosphorus dichloride.

EXAMPLE 4

Tert-butyl phosphorous dichloride is prepared by adding an equimolar amount of an ethereal suspension of tert-butyl magnesium chloride to a cooled solution of phosphorus trichloride in linear alkyl benzenes (a mixture of ($C_{10}$–$C_{12}$) alkyl benzenes) as solvent ("LAB"). After allowing the compounds to completely react, the ether is removed by distillation at room temperature. The remaining material is sublimed under vacuum to provide tert-butyl phosphorus dichloride in ca. 80% yield.

EXAMPLE 5

Iso-propyl arsenic dichloride is prepared according to the procedure of Example 4 except that arsenic trichloride is used instead of phosphorus trichloride and iso-propyl magnesium chloride is used instead of tert-butyl magnesium chloride.

EXAMPLE 6

Methyl arsenic dichloride is prepared according to the procedure of Example 2 except that iso-propyl magnesium chloride is replaced with methyl magnesium chloride.

EXAMPLE 7

Tert-butyl phosphorus dichloride (10 g, 0.06 mol) from Example 4 is dissolved in tri-n-propyl amine. This solution is then added dropwise to a stirred, room temperature solution of lithium aluminum hydride (4.7 g, 0.13 mol) in tri-n-propylamine (100 g). After the addition is complete, the reaction mixture is allowed to stir until the reaction is complete. The product, tert-butyl phosphine (or tert-butyl phosphorus dihydride), is removed by distillation at atmospheric pressure.

EXAMPLE 8

Ethyl arsenic dichloride (10 g, 0.07 mol) is dissolved in tri-n-propylamine. This solution is then added dropwise to a stirred, room temperature solution of lithium aluminum hydride (5.4 g, 0.14 mol) in tri-n-propylamine (100 g). After the addition is complete, the reaction mixture is allowed to stir until the reaction is complete. The product, ethyl arsine (or ethyl arsenic dihydride), is then removed by distillation at atmospheric pressure.

What is claimed is:

1. A method of preparing a Group VA metal dihalide compound comprising the step of reacting a Group VA metal trihalide with a reagent selected from the group consisting of an ($C_1$–$C_{10}$)alkyl lithium compound and a compound of the formula $R_nM^1X_{3-n}$ wherein each R is ($C_1$–$C_{10}$)alkyl, amino-substituted ($C_1$–$C_{10}$)alkyl, aryl or substituted aryl, $M^1$ is a Group IIIA metal, X is a halogen, and n is an integer from 1 to 3, in an organic solvent free of oxygen substitution.

2. A method for preparing a Group VA metal dihalide compound comprising the step of reacting a Group VA metal trihalide with a reagent selected from the group consisting of an organo lithium compound and a compound of the formula $R_nM^1X_{3-n}$ wherein each R is ($C_1$–$C_{10}$) alkyl, amino-substituted ($C_1$–$C_{10}$)alkyl, aryl or substituted aryl, $M^1$ is a Group IIIA metal, X is a halogen and n is an integer from 1 to 3, in the presence of a tertiary amine in an organic solvent free of oxygen substitution.

3. A method for preparing Group VA metal dihydride compounds comprising the step of reducing a Group VA metal dihalide in the presence of a tertiary amine in an organic solvent wherein the organic solvent is free of oxygen substitution.

4. The method of claim 2 or 3 wherein the tertiary amine has the formula $NR^4R^5R^6$, wherein $R^4$, $R^5$ and $R^6$ are independently selected from ($C_1$–$C_6$)alkyl, di ($C_1$–$C_6$) alkylamino-substituted-($C_1$–$C_6$)alkyl and phenyl, and wherein $R^4$ and $R^5$ may be taken together along with the nitrogen to which they are attached to form a 5–7 membered heterocyclic ring.

5. The method of claim 3 wherein the Group VA metal dihydride compounds have the formula $RMH_2$ or $H_2MR^1MH_2$, wherein R is ($C_1$–$C_{10}$)alkyl, amino-substituted ($C_1$–$C_{10}$)alkyl, aryl or substituted aryl; $R^1$ is ($C_1$–$C_{10}$) alkylene, ($C_8$–$C_{20}$)aralkylene or ($C_6$–$C_{20}$)arylene; and M is arsenic or phosphorous.

6. The method of claim 3 wherein the Group VA metal dihydride compounds are substantially free of ethereal solvents.

7. A method for manufacturing an electronic device comprising the step of depositing a film of a Group VA metal on an electronic device substrate comprising the steps of: a) conveying a Group VA metal dihydride compound or a Group VA metal dihalide compound in the gaseous phase to a deposition chamber containing the substrate; b) decomposing the Group VA metal dihydride compound or a Group VA metal dihalide compound in the deposition chamber; and c) depositing a film of Group VA metal on the substrate; wherein the Group VA metal dihydride compound is prepared by the method of claim 3.

8. A method for depositing a film of a Group VA metal on a substrate comprising the steps of: a) conveying a Group VA metal dihalide compound or a Group VA dihydride compound in the gaseous phase to a deposition chamber containing the substrate; b) decomposing the Group VA metal dihalide compound or the Group VA metal dihydride compound in the deposition chamber; and c) depositing a film of Group VA metal on the substrate; wherein the monoalkyl Group VA dihydride compound is prepared by the method of claim 3.

9. A method for depositing a film of a Group VA metal on a substrate comprising of the steps of: a) conveying a Group VA metal dihydride compound of the formula $RMH_2$ or $H_2MR^1MH_2$ in the gaseous phase to a deposition chamber containing the substrate; b) decomposing the Group VA metal compound in the deposition chamber; and c) depositing a film of the Group VA metal on the substrate; wherein the Group VA metal compound is substantially free of ethereal solvents; and wherein R is $(C_1-C_{10})$alkyl, amino-substituted $(C_1-C_{10})$alkyl, aryl or substituted aryl; $R^1$ is $(C_1-C_{10})$alkylene, $(C_8-C_{20})$aralkylene or $(C_6-C_{20})$arylene; and M is arsenic or phosphorus.

* * * * *